US012656004B2

(12) United States Patent
Umemura et al.

(10) Patent No.:  US 12,656,004 B2
(45) Date of Patent:  Jun. 16, 2026

(54) AIR CONDITIONER

(71) Applicant: DAIKIN INDUSTRIES, LTD., Osaka (JP)

(72) Inventors: Futoshi Umemura, Osaka (JP); Ryuji Seino, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 397 days.

(21) Appl. No.: 18/234,585

(22) Filed: Aug. 16, 2023

(65) Prior Publication Data

US 2023/0392804 A1    Dec. 7, 2023

Related U.S. Application Data

(63) Continuation of application No. PCT/JP2022/001588, filed on Jan. 18, 2022.

(30) Foreign Application Priority Data

Feb. 18, 2021    (JP) ................................. 2021-024284

(51) Int. Cl.
B01J 19/08        (2006.01)
A61L 9/20        (2006.01)
(Continued)

(52) U.S. Cl.
CPC .................. F24F 8/22 (2021.01); A61L 9/20 (2013.01); F24F 7/003 (2021.01); F24F 8/108 (2021.01); F24F 8/80 (2021.01); *A61L 2103/75* (2026.01); *A61L 2209/14* (2013.01); *A61L 2209/16* (2013.01)

(58) Field of Classification Search
CPC ..... A61L 9/00; A61L 9/18; A61L 9/20; A61L 9/205; A61L 2209/14
(Continued)

(56) References Cited

U.S. PATENT DOCUMENTS 5,997,619 A    12/1999  Knuth et al.
6,579,352 B1    6/2003  Tanaka et al.
(Continued)

FOREIGN PATENT DOCUMENTS

CN          205843000 U    12/2016
EP          3 593 825 A1    1/2020
(Continued)

OTHER PUBLICATIONS

Extended European Search Report for European Application No. 22755804.6, dated Jun. 12, 2024.
(Continued)

*Primary Examiner* — Monzer R Chorbaji
(74) *Attorney, Agent, or Firm* — Birch, Stewart, Kolasch & Birch, LLP

(57)            ABSTRACT

An air conditioner includes a casing provided with an air passage having a suction port and a blow-out port, a fan that is disposed in the air passage and blows out, from the blow-out port, air sucked from the suction port, a primary filter disposed in the air passage, and a secondary filter disposed downstream of the primary filter in the air passage. The secondary filter is finer than the primary filter and has antiviral properties or antibacterial properties. This allows sufficient sterilization of indoor spaces.

5 Claims, 7 Drawing Sheets

(51) Int. Cl.

| | |
|---|---|
| *B01D 53/02* | (2006.01) |
| *B03C 3/00* | (2006.01) |
| *B60H 3/06* | (2006.01) |
| *F24F 7/003* | (2021.01) |
| *F24F 8/108* | (2021.01) |
| *F24F 8/22* | (2021.01) |
| *F24F 8/80* | (2021.01) |
| *A61L 103/75* | (2026.01) |

(58) Field of Classification Search
USPC .......... 422/24, 186.04; 96/60, 62, 121, 134; 204/164; 454/158
See application file for complete search history.

(56) References Cited

U.S. PATENT DOCUMENTS

| | | | |
|---|---|---|---|
| 2004/0221554 A1 | 11/2004 | Iijima et al. | |
| 2009/0120781 A1* | 5/2009 | Motegi ..................... | B03C 3/41 |
| | | | 204/164 |
| 2020/0061231 A1 | 2/2020 | Jeong et al. | |

FOREIGN PATENT DOCUMENTS

| | | | | | |
|---|---|---|---|---|---|
| JP | 2004-61078 | A | 2/2004 | | |
| JP | 2005-342509 | A | 12/2005 | | |
| JP | 2009-248031 | A | 10/2009 | | |
| JP | 2010240053 | | * 10/2010 | .............. | A61L 9/00 |
| JP | 2010240053 | A | * 10/2010 | .............. | A61L 9/00 |
| JP | 2016-138718 | A | 8/2016 | | |
| JP | 2018-185074 | A | 11/2018 | | |
| WO | WO 98/04334 | A1 | 2/1998 | | |
| WO | WO 02/078754 | A1 | 10/2002 | | |

OTHER PUBLICATIONS

English translation of International Preliminary Report on Patentability and Written Opinion of the International Searching Authority for International Application No. PCT/JP2022/001588, dated Aug. 31, 2023.

International Search Report (PCT/ISA/210) issued in PCT/JP2022/001588 mailed on Mar. 15, 2022.

* cited by examiner

AIR CONDITIONER

CROSS REFERENCE TO RELATED APPLICATIONS

This application is a Continuation of PCT International Application No. PCT/JP2022/001588, filed on Jan. 18, 2022, which claims priority under 35 U.S.C. § 119(a) to Patent Application No. 2021-024284, filed in Japan on Feb. 18, 2021, all of which are hereby expressly incorporated by reference into the present application.

TECHNICAL FIELD

The present disclosure relates to an air conditioner.

BACKGROUND ART

There has been disclosed an air conditioner including an ultraviolet lamp (see, for example, JP 2004-61078 A) The ultraviolet lamp is disposed upwind of a dust collection filter installed in a main body case of the air conditioner, and irradiates the filter with ultraviolet light.

In the air conditioner described above, the ultraviolet lamp irradiates a windward surface of the dust collecting filter with the ultraviolet light to kill viruses and the like attached to the windward surface of the dust collecting filter.

SUMMARY

An air conditioner of the present disclosure includes:
a casing provided with an air passage having a suction port and a blow-out port;
a fan that is disposed in the air passage and blows out, from the blow-out port, air sucked from the suction port;
a primary filter disposed in the air passage; and
a secondary filter disposed downstream of the primary filter in the air passage, in which
the secondary filter is finer than the primary filter and has antiviral properties or antibacterial properties.

DESCRIPTION OF EMBODIMENT

Figure 1:
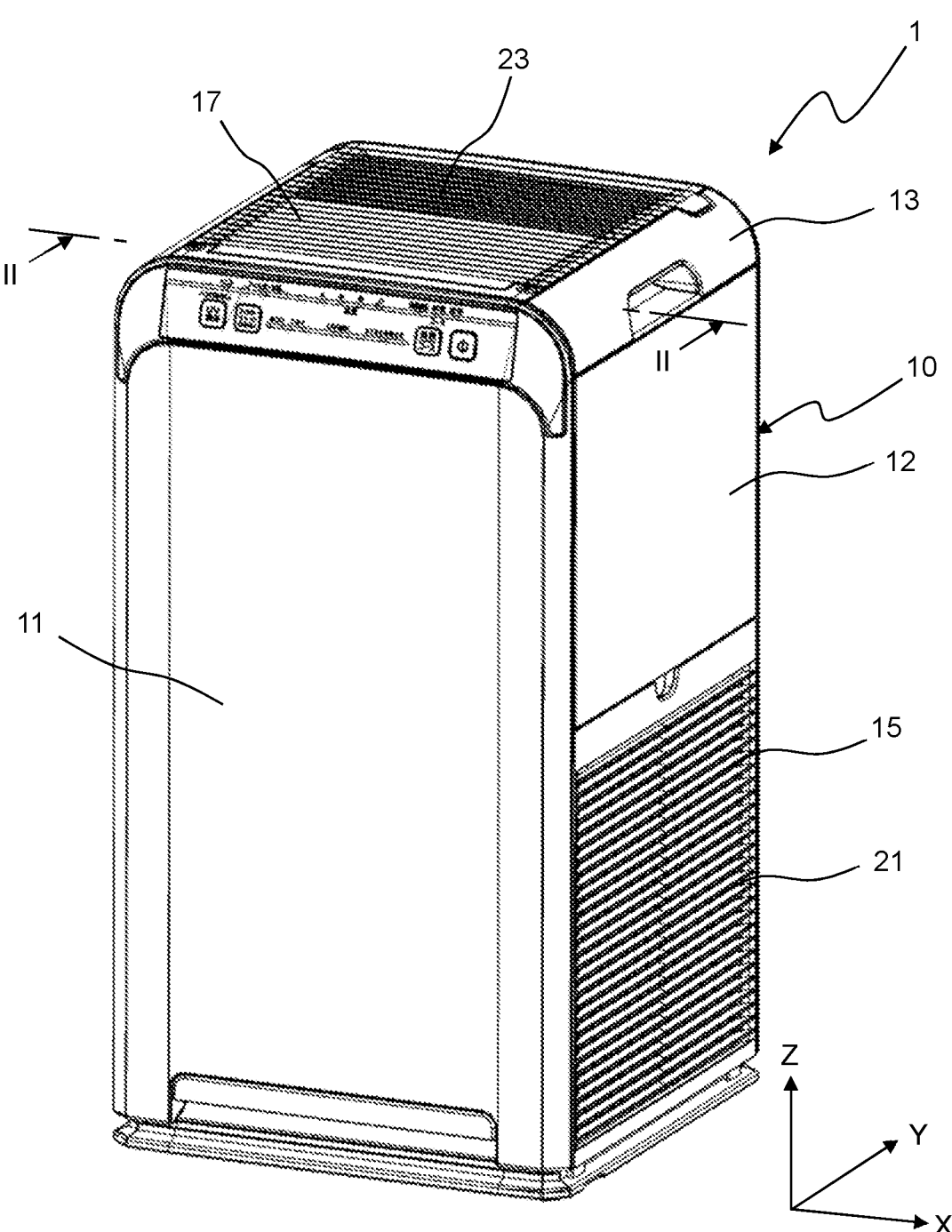
FIG. 1 is an external perspective view of an air purifier according to an embodiment of the present disclosure.

Hereinafter, an embodiment will be described. It should be noted that in the drawings, the same reference numerals represent the same or corresponding parts. In addition, the dimensions on the drawings, such as lengths, widths, thicknesses, and depths, are appropriately changed from actual scales for clarity and simplification of the drawings, and do not represent actual relative dimensions. In the drawings, a left-right direction is defined as an X-axis direction, a front-rear direction is defined as a Y-axis direction, and an up-down direction is defined as a Z-axis direction.

Figure 2:
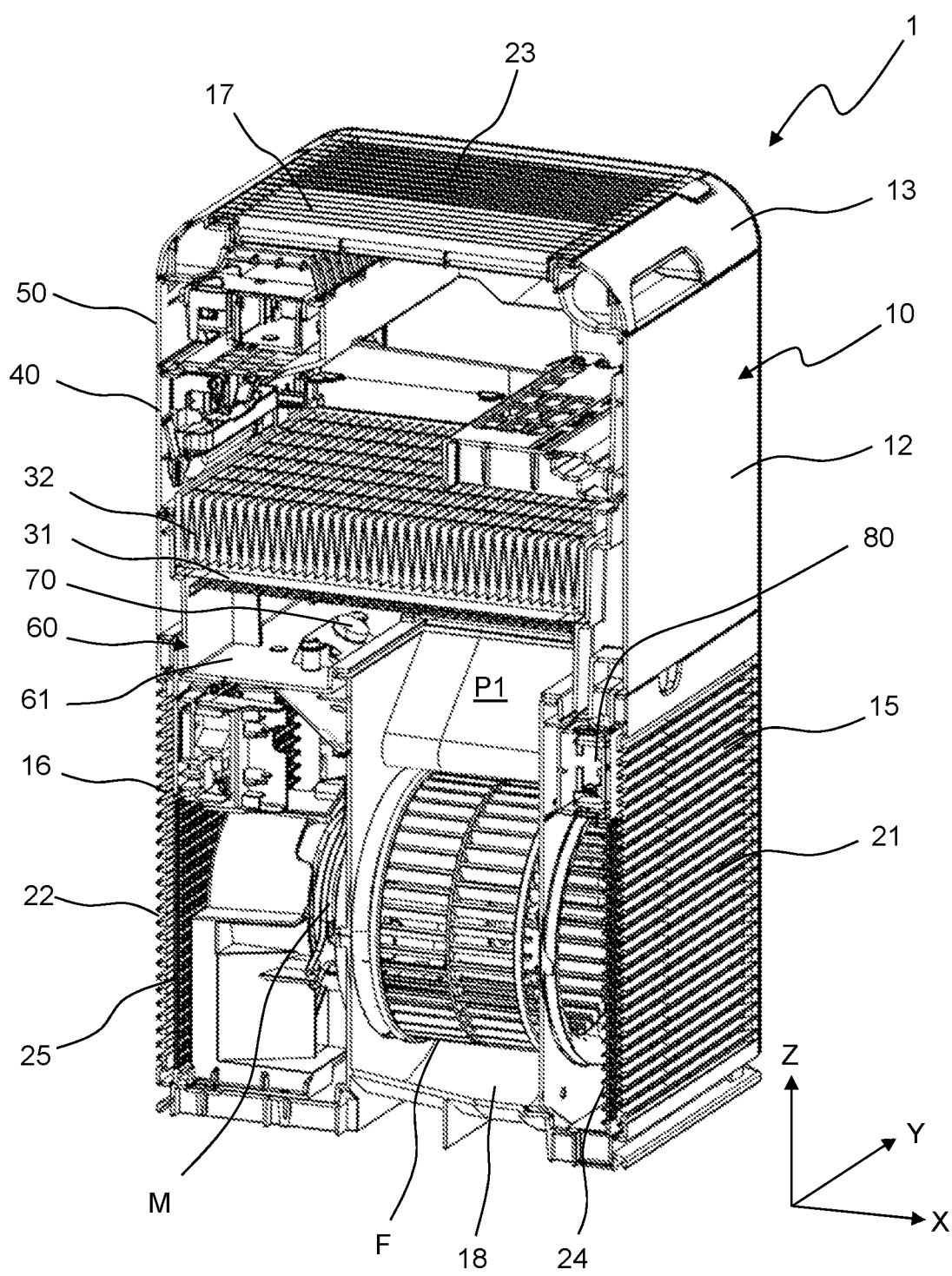
FIG. 2 is a perspective view of a cross section taken along a line II-II in FIG. 1.

FIG. 1 is an external perspective view of an air purifier 1 according to an embodiment of the present disclosure as viewed from front and obliquely above, and FIG. 2 is a perspective view of a cross section taken along a line II-II in FIG. 1. The air purifier 1 of this embodiment is an example of an air conditioner.

As illustrated in FIGS. 1 and 2, the air purifier 1 includes a casing 10 with a rectangular parallelepiped shape, a fan F, a primary filter 31, and a secondary filter 32. The casing 10 is provided with an air passage P1 having a right suction port 21, a left suction port 22, and a blow-out port 23. The fan F is disposed in the air passage P1 and blows out, through the blow-out port 23, air sucked from the right suction port 21 and the left suction port 22. The primary filter 31 is disposed in the air passage P1. The secondary filter 32 is disposed downstream of the primary filter 31 in the air passage P1.

The air purifier 1 further includes an irradiator 70 that irradiates an upstream surface of the primary filter 31 with ultraviolet light, and a streamer unit 80 disposed upstream of the primary filter 31 in the air passage P1. The streamer unit 80 is an example of a generator that generates active species.

The casing 10 includes a front panel 11, left and right side panels 12, a top panel 13, a rear panel 14 (illustrated in FIG. 5), a right suction grille 15 detachably attached below the right side panel 12, a left suction grille 16 detachably attached below the left side panel 12, and a blow-out grille 17 detachably attached to the top panel 13.

The right suction port 21 is covered with the right suction grille 15 having a grid shape so as to allow air to flow through. The left suction port 22 is covered with the left suction grille 16 having a grid shape so as to allow air to flow through. The blow-out port 23 is covered with the blow-out grille 17 having a grid shape so as to allow air to flow through.

A resin case 40 to which a deodorizing filter (not illustrated) is attachable is detachably attached to the casing 10. Further, an upper frame 50 is fitted into the casing 10 above the resin case 40.

Note that the casing 10 is configured to prevent the ultraviolet light from leaking out from the irradiator 70 provided in the casing 10 (in accordance with IEC standard 60335-2-40 (illuminance of 0.2 $\mu$W/cm$^2$ or less at a distance of 0.3 m from an outer contour)).

The fan F is a sirocco fan that sucks air from both sides in an axial direction and blows the air radially outward. The fan F is installed in a fan housing 18 having left and right suction ports 18$a$ and 18$b$ (illustrated in FIG. 3 and FIG. 4) and a scroll 18$c$. The fan housing 18 is provided with a blow-out port 18$d$ through which air sucked from the suction ports 18$a$ and 18$b$ blows upward. A motor M is further provided, the motor M being connected to a left side of the fan F via a shaft 19 (illustrated in FIG. 4).

In the casing 10, a lower frame 60 is disposed above the fan housing 18, the lower frame 60 having a box shape and being opened upward. The lower frame 60 and the upper frame 50 form a space in which the resin case 40 is installed.

The irradiator 70 that irradiates the upstream surface the primary filter 31 with the ultraviolet light is attached to a bottom portion 61 of the lower frame 60. The bottom portion 61 of the lower frame 60 is an example of a partitioning member.

The primary filter 31 is a filter capable of removing particles having a particle diameter of 10 $\mu$m to 50 $\mu$m. A thickness of the primary filter 31 is set so as to allow the ultraviolet light from the irradiator 70 to reach a downstream surface of the primary filter 31 (for example, a thickness of about 5 mm to 10 mm). Here, the irradiator 70 includes a light emitting diode (LED) that emits deep ultraviolet light UVC in a wavelength region of 100 nm to 280 nm.

Note that, in the present embodiment, the irradiator 70 that emits the deep ultraviolet light UVC in the wavelength range of 100 nm to 280 nm is used, but any irradiator that emits ultraviolet light within a wavelength range of 100 nm to 400 nm may be used. Alternatively, an ultraviolet lamp or the like may be used as the irradiator.

The secondary filter 32 is a filter having a pleated structure, and is a filter that traps particles having a particle diameter of 0.7 μm. For example, the filter may be a high efficiency particulate air (HEPA) filter that traps 99.97% or more of particles having a particle diameter of 0.3 μm or a medium efficiency particulate air filter that traps particles having a particle diameter of 0.4 μm to 0.7 μm. The secondary filter 32 is impregnated with a chemical agent exhibiting antiviral properties. For example, a lytic enzyme that destroys the envelopes of viruses to inactivate the viruses is used as the chemical agent.

Note that the secondary filter may be impregnated with a chemical agent exhibiting antibacterial properties to inhibit the growth of bacteria, or both the chemical agent exhibiting antiviral properties and the chemical agent exhibiting antibacterial properties may be used. Examples of the chemical agent exhibiting antiviral properties and antibacterial properties include Ag, an enzyme, ammonia, and the like, and a chemical agent containing a mixture of at least two of Ag, an enzyme, ammonia, and the like may be used.

Net-like pre-filters 24 and 25 for removing relatively large dust are attached to a leeward surface of the right suction grille 15 and a leeward surface of the left suction grille 16, respectively. The pre-filters 24 and 25 are each disposed upstream of the primary filter 31 in the air passage P1. The pre-filters 24 and 25 trap dust larger than particles to be trapped by the primary filter 31.

The air passage P1 is formed in the casing 10. Air sucked in the air passage P1 from the right suction port 21 and the left suction port 22 blows out from the blow-out port 23 via the fan F, the primary filter 31, and the secondary filter 32

Figure 3:
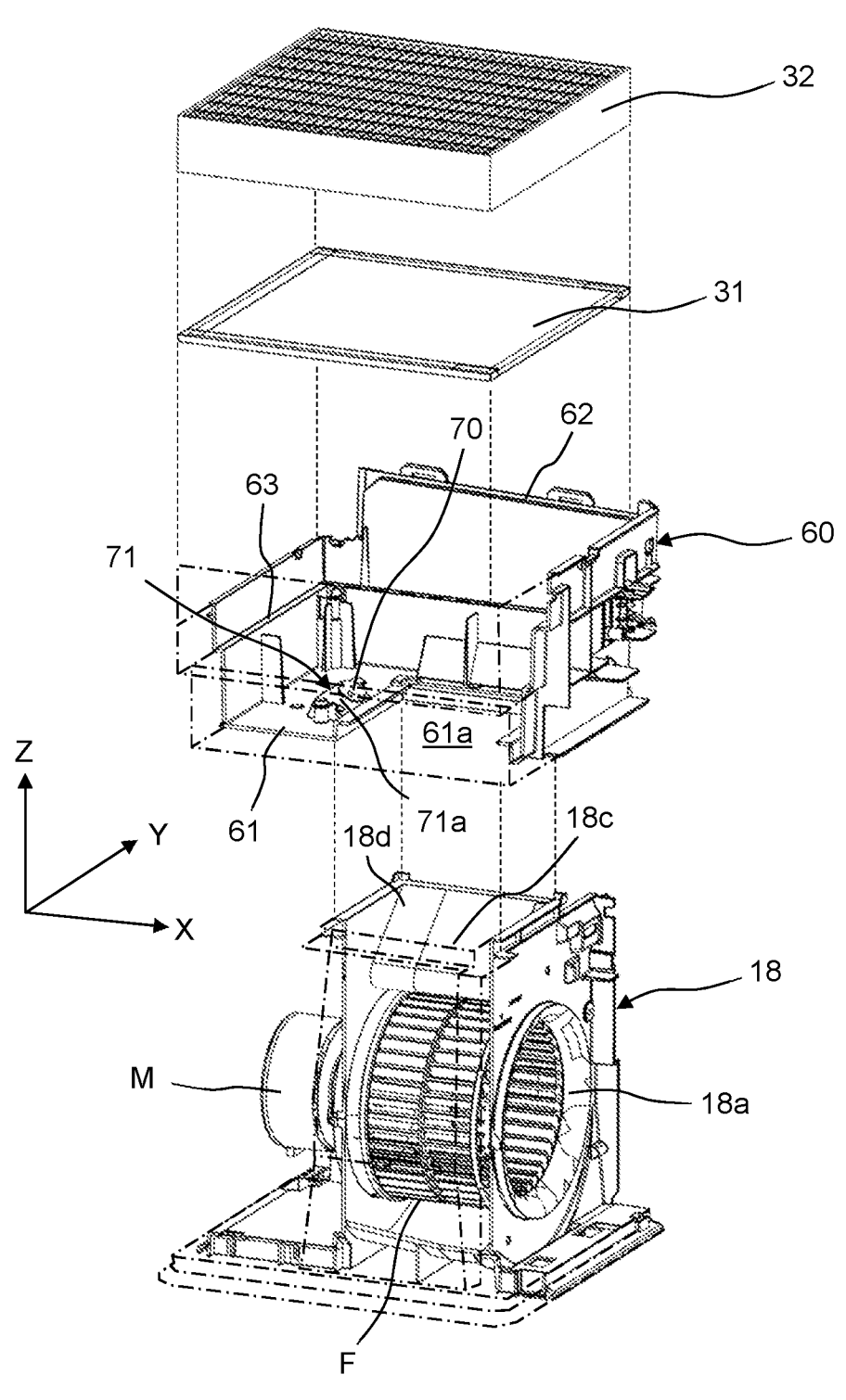
FIG. 3 is an exploded perspective view illustrating a configuration of a main part of the air purifier.

FIG. 3 is an exploded perspective view illustrating a configuration of a main part of the air purifier 1. Note that, in FIG. 3, the lower frame 60 and the fan housing 18 are each illustrated as a cross section taken along the line II-II in FIG. 1.

As illustrated in FIG. 3, the lower frame 60 includes the bottom portion 61 having an opening 61a to which the blow-out port 18d of the fan housing 18 is connected, and a wall portion 62 extending upward from an outer peripheral edge of the bottom portion 61. In the wall portion 62, a peripheral step 63 is formed at a distance from the bottom portion 61. The primary filter 31 and the secondary filter 32 are supported by an upper surface of the peripheral step 63 with the secondary filter 32 stacked on top of the primary filter 31.

A base 71 having an inclined surface 71a is provided on a surface of the bottom portion 61 of the lower frame 60 facing the primary filter 31. The irradiator 70 is attached to the inclined surface 71a of the base 71.

Figure 4:
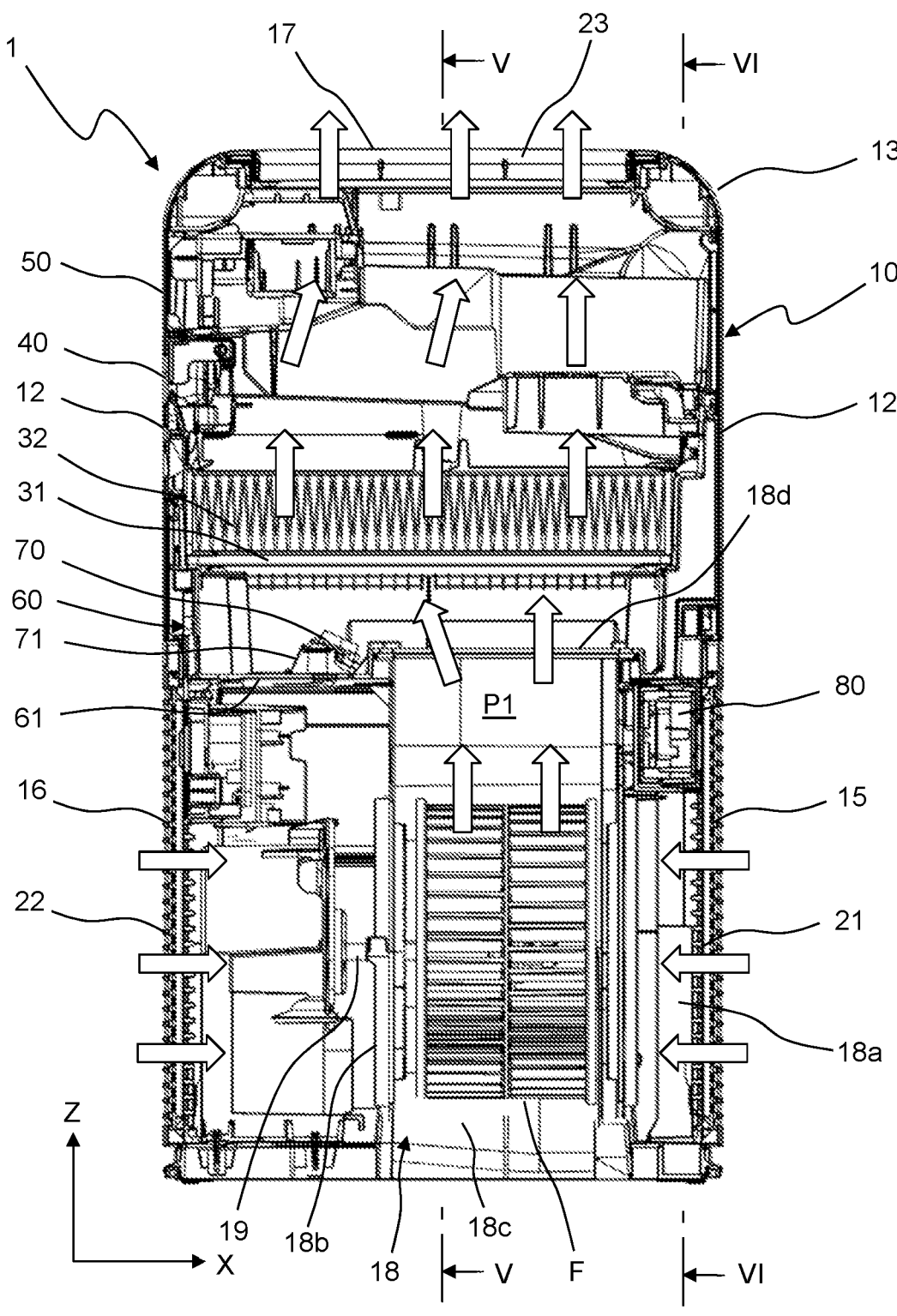
FIG. 4 is a cross-sectional view taken along the line II-II in FIG. 1.

FIG. 4 is a cross-sectional view taken along the line II-II in FIG. 1. In FIG. 4, arrows indicate the flow of air through the air passage P1.

As illustrated in FIG. 4, when the fan F is driven by the motor M, air sucked by the fan F from the right suction port

21 and the left suction port 22 blows upward from the fan F and then blows upward from the blow-out port 23 through the primary filter 31 and the secondary filter 32.

Figure 5:
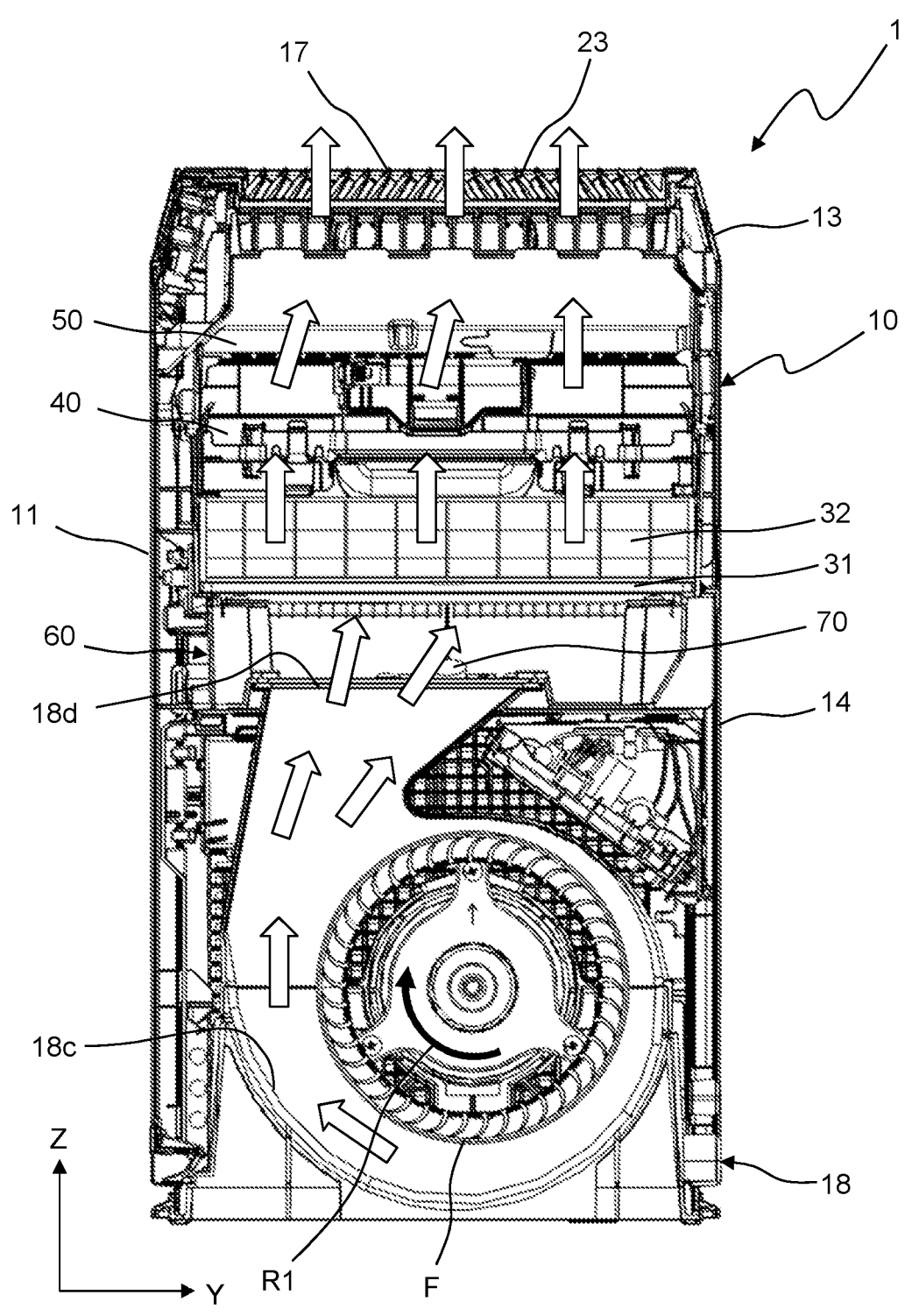
FIG. 5 is a cross-sectional view taken along a line V-V in FIG. 4.

FIG. 5 is a cross-sectional view taken along a line V-V in FIG. 4, and in FIG. 5, when the fan F rotates in a clockwise direction (arrow R1), air sucked from both sides in a direction perpendicular to the paper surface blows radially outward of the fan F and is straightened by the scroll 18c of the fan housing 18 to blow upward from the blow-out port 18d.

Figure 6:
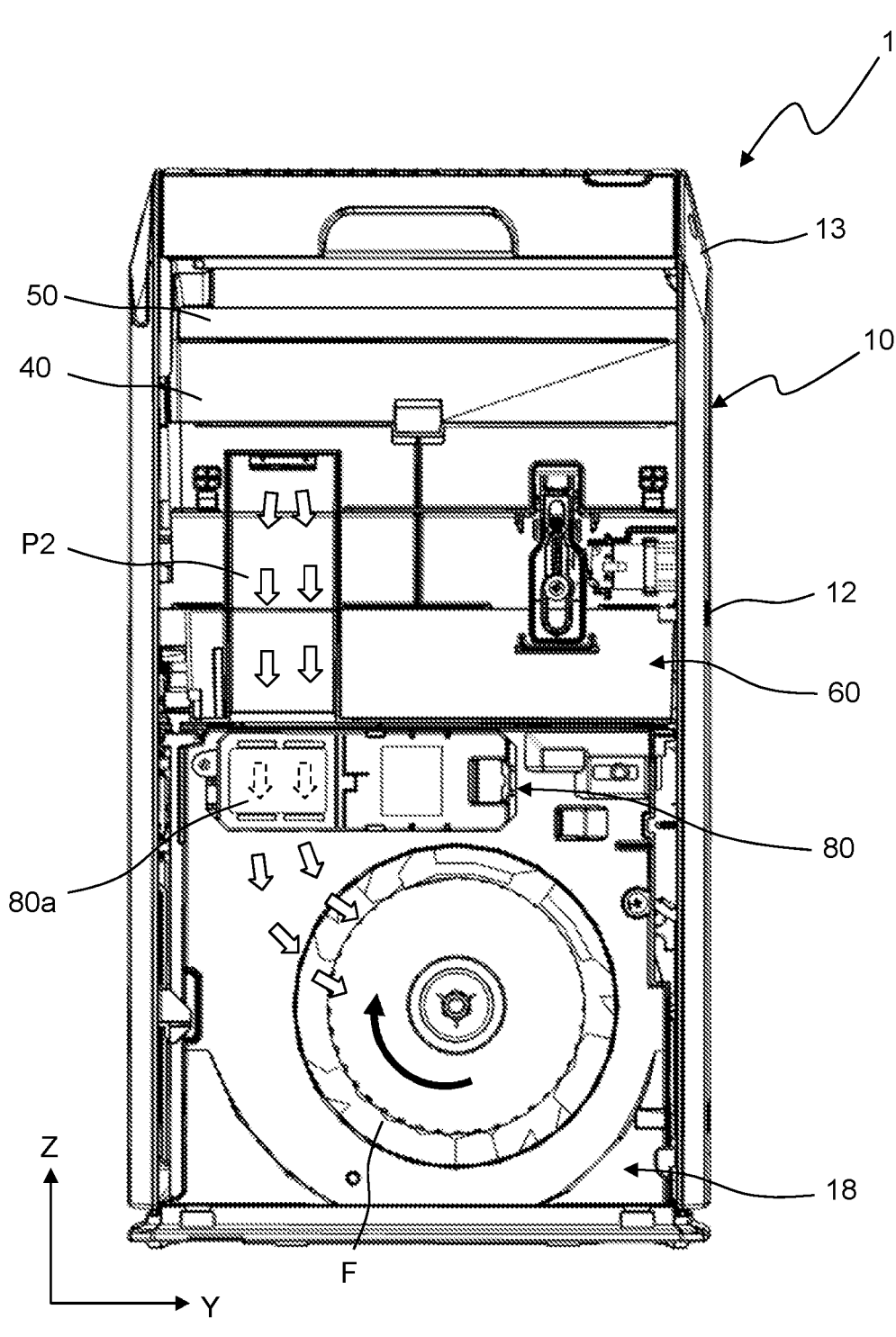
FIG. 6 is a cross-sectional view taken along a line VI-VI in FIG. 4.

FIG. 6 is a cross-sectional view taken along a line VI-VI in FIG. 4, and a second air passage P2 is formed along the up-down direction on a side surface of the lower frame 60. The second air passage P2 has an upper end connected to a downstream side of the secondary filter 32 in the air passage P1, and has a lower end connected to a discharge unit 80a of the streamer unit 80. The streamer unit 80 causes the discharge unit 80a to perform streamer discharge to generate low-temperature plasma, which generates highly reactive active species (fast electrons, ions, radicals, ozone, or the like) in the air.

Purified air from the downstream side of the secondary filter 32 in the air passage P1 is supplied to the streamer unit 80 through the second air passage P2, and is sucked into the fan F together with the active species generated by the discharge unit 80a of the streamer unit 80. This active species can sterilize viruses and bacteria in air sucked from the right suction port 21 and the left suction port 22 and decompose allergen substances and odors in the air. Since the purified air is supplied to the discharge unit 80a of the streamer unit 80, it is possible to reduce the adhesion of impurities to a needle of the discharge unit 80a and suppress deterioration in the active species generation performance of the streamer unit 80.

Note that the active species generated by the streamer unit 80 spread throughout the air passage P1, so that it is possible to disinfect components such as the fan F located upstream of the primary filter 31 in the air passage P1. Further, the active species generated by the streamer unit 80 are supplied to all over the primary filter 31, so that it is possible to disinfect a part of the primary filter 31 where the illuminance of the ultraviolet light emitted from the irradiator 70 is low. Furthermore, the active species generated by the streamer unit 80 spread deep into folds of the secondary filter 32 having a pleated structure, producing a disinfection effect, so that it is possible to increase disinfection performance.

Figure 7:
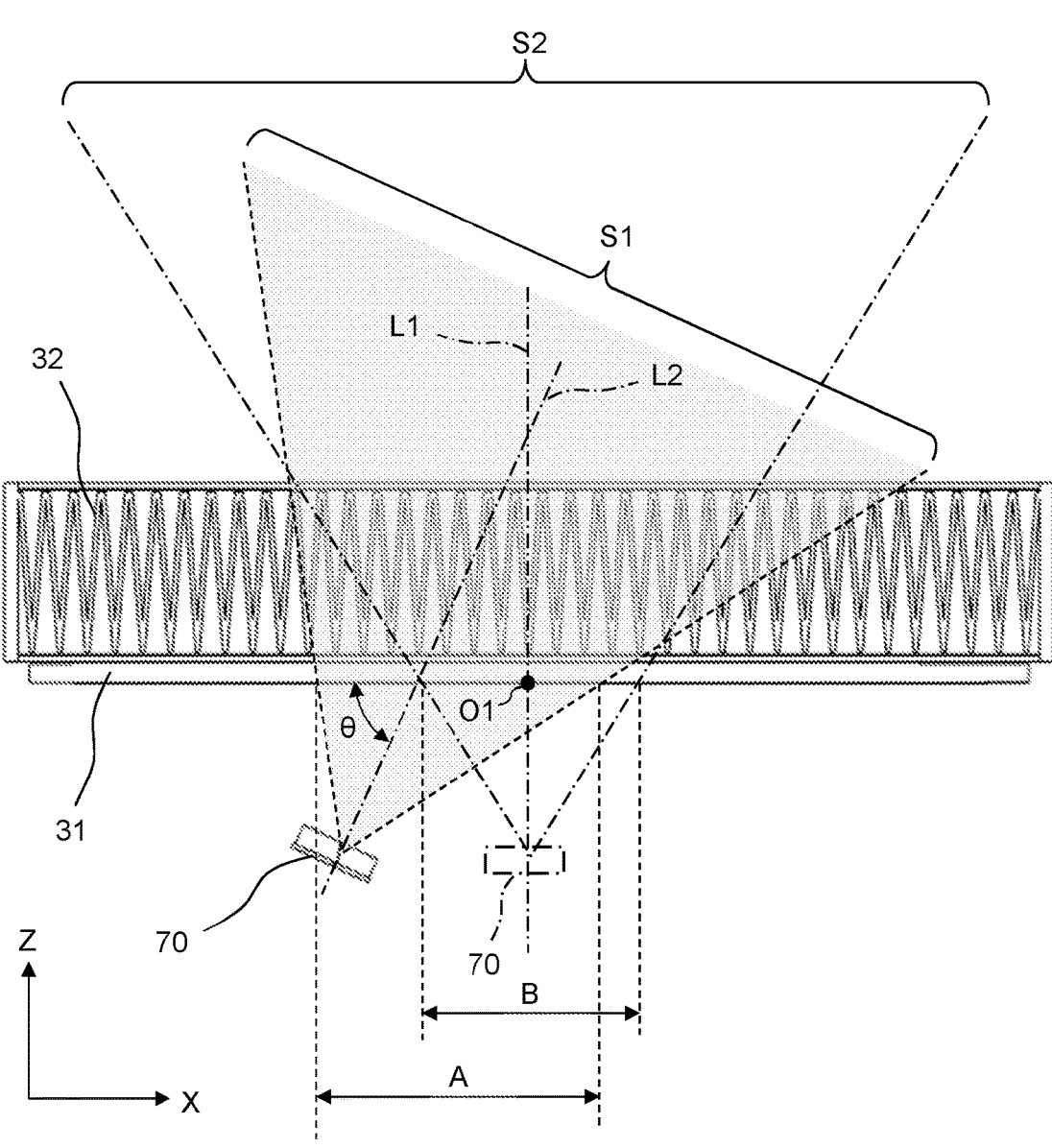
FIG. 7 is a diagram schematically illustrating an irradiation region of an irradiator.

FIG. 7 illustrates an irradiation region of the irradiator 70, and, as illustrated in FIG. 7, the irradiator 70 is disposed at a distance in the X-axis direction from a center line L1 passing through a center O1 of the primary filter 31 and orthogonal to the primary filter 31.

An optical axis L2 of the ultraviolet light emitted from the irradiator 70 is inclined relative to a plane orthogonal to a thickness direction of the primary filter 31. In the present embodiment, an angle θ formed by the optical axis L2 of the ultraviolet light emitted from the irradiator 70 and the plane orthogonal to the thickness direction of the primary filter 31 is about 60 degrees.

The optical axis L2 of the ultraviolet light emitted from the irradiator 70 passes through a center portion of the primary filter 31. Here, the center portion of the primary filter 31 is a region extending from the center O1 of the primary filter 31 toward an outer edge of the primary filter 31 by ½ or less of a distance from the center O1 to the outer edge.

The center O1 of the primary filter 31 falls within an irradiation region S1 having a relative luminous intensity in directivity of the irradiator 70 greater than or equal to 50%. Note that a region of the primary filter 31 outside the irradiation region S1 is also irradiated with ultraviolet light having a relative luminous intensity of less than 50% within a range of the directivity of the irradiator 70. In the irradiator 70, a directivity angle for the irradiation region S1 is, for example, ±65 degrees, which makes a region that can be irradiated wider.

Here, with an irradiation area of the primary filter 31 in the irradiation region S1 of the irradiator 70 denoted as A, when the irradiator 70 is disposed such that the optical axis L2 of the irradiator 70 coincides with the center line L1 orthogonal to the primary filter 31, an irradiation area B of the primary filter 31 in an irradiation region S2 of the irradiator 70 is smaller than the irradiation area A. In the present embodiment, the irradiation area A of the primary filter 31 is about 1.6 times the irradiation area B.

As described above, the optical axis L2 of the ultraviolet light emitted from the irradiator 70 is inclined relative to the plane orthogonal to the thickness direction of the primary filter 31, so that it is possible to increase the irradiation region of the primary filter 31 irradiated with the ultraviolet light without increasing a distance in the Z-axis direction between the irradiator 70 and the primary filter 31, which allows efficient disinfection of the primary filter 31.

The air purifier 1 having the above-described configuration causes the primary filter 31 to trap dust contained in the air sucked from the right suction port 21 and the left suction port 22 by the fan F and further causes the secondary filter 32 finer than the primary filter 31 to trap viruses together with the remaining small amount of dust. The primary filter 31 first traps dust, so that deterioration in sterilization performance of the secondary filter 32 caused by dust is suppressed, and viruses trapped by the secondary filter 32 are efficiently inactivated by the secondary filter 32 having antiviral properties. It is therefore possible to quickly disinfect an indoor space.

With a conventional air purifier using a normal HEPA filter as the secondary filter and including neither the primary filter nor the irradiator, it has taken about 2.5 hours to disinfect 99% of an eight-tatami-mat room (about 26.4 m²) at an air volume of 5.0 m/min, whereas with the air purifier 1 of the present embodiment, 99% of the room has been successfully disinfected in about 30 minutes at an air volume of 5.0 m/min under the same conditions.

Irradiating the upstream surface of the primary filter 31 with the ultraviolet light emitted from the irradiator 70 also allows the ultraviolet light to inactivate viruses attached to dust trapped by the primary filter 31, so that it is possible to increase the sterilization performance.

The ultraviolet light emitted from the irradiator 70 can reach the downstream surface of the primary filter 31, so that it is possible to irradiate the entirety of the thickness of the primary filter 31 with the ultraviolet light and thus increase the sterilization performance of the primary filter 31.

The secondary filter 32 is a filter having a pleated structure, so that it is possible to make an area for trapping viruses larger and thus increase the sterilization performance of the secondary filter 32 having antiviral properties. Even when the secondary filter 32 having a pleated structure is irradiated with ultraviolet light, the ultraviolet light is applied only to a part of the windward surface of the secondary filter 32, and viruses attached to the folds of the pleats cannot be inactivated; however, it is possible to inactivate, using the secondary filter 32 impregnated with a chemical agent exhibiting antiviral properties, the viruses attached to the folds of the pleats.

Relatively large dust contained in the air sucked from the right suction port 21 and the left suction port 22 by the fan F is trapped by the pre-filters 24 and 25 each disposed upstream of the primary filter 31 in the air passage P1, so that it is possible to prevent the primary filter 31 from being clogged.

The bottom portion 61 (partitioning member) of the lower frame 60 is provided upstream of the primary filter 31 and downstream of the fan F, and the irradiator 70 is attached to the downstream surface of the bottom portion 61 of the lower frame 60, so that the air from the fan F is prevented from directly striking the irradiator 70, and it is therefore possible to reduce the adhesion of dust to the irradiator 70.

The base 71 is provided on the surface of the bottom portion 61 of the lower frame 60 facing the primary filter 31, and the irradiator 70 is attached to the inclined surface 71a of the base 71, so that it is possible to easily attach the irradiator 70 with the optical axis L2 of the irradiator 70 inclined relative to the plane orthogonal to the thickness direction of the primary filter 31.

The air from the fan F blows out from the opening provided in the bottom portion 61 of the lower frame 60 toward the primary filter 31, so that the air from the fan F is prevented from directly striking the irradiator 70, and it is therefore possible to reduce the adhesion of dust to the irradiator 70.

The ultraviolet light emitted from the irradiator 70 passes through the center portion of the primary filter 31, so that it is possible to irradiate the entirety of the primary filter 31 or almost the entirety of the primary filter 31 with the ultraviolet light without uneven irradiation on the primary filter 31.

The irradiator 70 is disposed out of alignment with the center line L1 passing through the center O1 of the primary filter 31 and orthogonal to the primary filter 31, so that it is possible to prevent the irradiator 70 from hindering the flow of air through the primary filter 31.

The center O1 of the primary filter 31 falls within the irradiation region having a relative luminous intensity in the directivity of the irradiator 70 greater than or equal to 50%, so that it is possible to irradiate the entirety of the primary filter 31 or almost the entirety of the primary filter 31 with the ultraviolet light without uneven irradiation on the primary filter 31.

One irradiator 70 can irradiate the entirety of the primary filter 31 or almost the entirety of the primary filter 31 with the ultraviolet light without an increase in the distance between the irradiator 70 and the primary filter 31, so that it is possible to reduce the cost and the power consumption as compared with a case where a plurality of irradiators 70 are used.

In the above-described embodiment, the air purifier 1 has been described as an example of the air conditioner, but the present disclosure may be applied to an air conditioner having a cooling function or a heating function.

In the above-described embodiment, the air purifier 1 in which the fan F is disposed upstream of the primary filter 31 and the secondary filter 32 has been described, but the fan may be disposed downstream of the primary filter and the secondary filter.

Although a specific embodiment of the present disclosure has been described, the present disclosure is not limited to the above-described embodiment, and various modifications can be made within the scope of the present disclosure.

REFERENCE SIGNS LIST

1 air purifier
10 casing 11 front panel
12 side panel
13 top panel
14 rear panel
15 right suction grille
16 left suction grille
17 blow-out grille
18 fan housing
18*a*, 18*b* suction port
18*c* scroll
18*d* blow-out port
19 shaft
21 right suction port
22 left suction port
23 blow-out port
24, 25 pre-filter
31 primary filter
32 secondary filter
40 resin case
50 upper frame
60 lower frame
61 bottom portion (partitioning member)
61*a* opening
62 wall portion
63 peripheral step
70 irradiation unit
71 base
71*a* inclined surface
streamer unit
discharge unit
F fan
M motor
P1 air passage
P2 second air passage

What is claimed is:

1. An air conditioner comprising:

a casing provided with an air passage having a suction port and a blow-out port;

a fan that is disposed in the air passage and blows out, from the blow-out port, air sucked from the suction port;

a primary filter disposed in the air passage capable of removing first particles having particle diameters of 10 μm to 50 μm; and a secondary filter disposed downstream of the primary filter in the air passage, wherein the secondary filter is capable of removing second particles having particle diameters smaller than those of the first particles and has antiviral properties or antibacterial properties, and the air conditioner further comprises an irradiator that irradiates an upstream surface of the primary filter with ultraviolet light.

2. The air conditioner according to claim 1, wherein a thickness of the primary filter is set so as to allow the ultraviolet light emitted from the irradiator to reach a downstream surface of the primary filter.

3. The air conditioner according to claim 1, wherein the secondary filter is a filter having a pleated structure.

4. The air conditioner according to claim 1, further comprising a pre-filter disposed upstream of the primary filter in the air passage.

5. The air conditioner according to claim 1, further comprising a generator that generates active species, wherein the active species are supplied from the generator to the primary filter.

* * * * *